United States Patent
Dinh et al.

(10) Patent No.: US 9,399,054 B2
(45) Date of Patent: Jul. 26, 2016

(54) COMPOSITIONS FOR DELIVERING PEPTIDE YY AND PYY AGONISTS

(75) Inventors: Steven Dinh, Briarcliff Manor, NY (US); Huaizhen Wang, Chappaqua, NY (US); Maria Isabel Gomez-Orellana, New Rochelle, NY (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 2109 days.

(21) Appl. No.: 11/571,862

(22) PCT Filed: Jul. 12, 2005

(86) PCT No.: PCT/US2005/024599
§ 371 (c)(1),
(2), (4) Date: Jul. 1, 2009

(87) PCT Pub. No.: WO2006/017251
PCT Pub. Date: Feb. 16, 2006

(65) Prior Publication Data
US 2011/0183898 A1    Jul. 28, 2011

Related U.S. Application Data

(60) Provisional application No. 60/587,751, filed on Jul. 12, 2004.

(51) Int. Cl.
*A61K 47/48* (2006.01)
*A61K 38/22* (2006.01)
*A61K 9/00* (2006.01)
*A61K 9/20* (2006.01)

(52) U.S. Cl.
CPC .............. *A61K 38/22* (2013.01); *A61K 9/0056* (2013.01); *A61K 9/2072* (2013.01)

(58) Field of Classification Search
None
See application file for complete search history.

(56) References Cited

U.S. PATENT DOCUMENTS

| 6,242,495 B1 | 6/2001 | Leone-Bay et al. |
| 7,459,432 B2 * | 12/2008 | Cowley et al. ................ 514/1.1 |
| 2004/0115135 A1 | 6/2004 | Quay |

FOREIGN PATENT DOCUMENTS

| JP | 2001131090 A | | 11/2002 |
| WO | WO-0048589 A1 | | 8/2000 |
| WO | WO-0132596 A1 | | 5/2001 |
| WO | WO-0170219 A1 | | 9/2001 |
| WO | WO-02/070438 | * | 9/2002 |
| WO | WO-02070438 A2 | | 9/2002 |
| WO | WO-03057170 A2 | | 7/2003 |
| WO | WO -2004056314 | * | 7/2004 |
| WO | WO 2004056314 | * | 7/2004 |
| WO | WO-2004056314 A2 | | 7/2004 |
| WO | WO-2004104018 A2 | | 12/2004 |

OTHER PUBLICATIONS

Leone-Bay, Polymer Preprints (American Chemical Society, Division of Polymer Chemistry) (1999), 40(1), 314-315.*
Batterham, et al., Gut Hormone PYY3-36 Physiologically Inhibits Food Intake, Nature, vol. 418, Aug. 8, 2002, pp. 650-654.
International Search Report issued in PCT/US05/24599 on Mar. 4, 2008.
Supplementary European Search Report issued in EP 05770299 on Jul. 27, 2012.

* cited by examiner

*Primary Examiner* — Satyanarayana R Gudibande
(74) *Attorney, Agent, or Firm* — Blank Rome LLP

(57) ABSTRACT

The present invention provides a composition (e.g., a pharmaceutical composition) comprising at least one delivery agent compound and at least one of peptide YY (PYY) and a PYY agonist. Preferably, the composition includes a therapeutically effective amount of peptide YY or the PYY agonist and the delivery agent compound. The composition of the present invention facilitates the delivery of PYY, a PYY agonist, or a mixture thereof and increases its bioavailability compared to administration without the delivery agent compound. PPY and PYY agonists possess activity as agents to reduce nutrient availability, including reduction of food intake.

7 Claims, 1 Drawing Sheet

Buccal Tablet Administration of PYY in Dogs
PYY/SNAD: 0.1/10 mg/kg
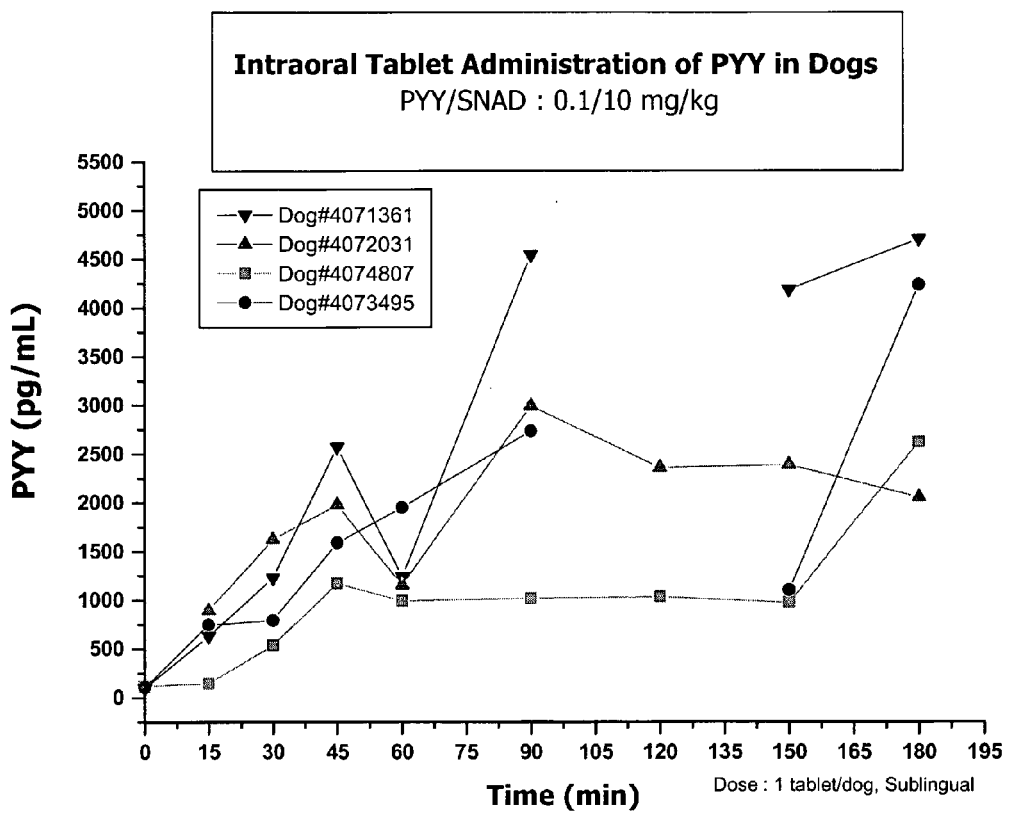

COMPOSITIONS FOR DELIVERING PEPTIDE YY AND PYY AGONISTS

This application claims the priority date of and incorporates by reference U.S. Provisional Patent Application No. 60/587,751, filed Jul. 12, 2004, and incorporates by reference U.S. patent application Ser. No. 10/846,954, filed May 14, 2004, U.S. Provisional Patent Application No. 60/470,905, filed May 14, 2003, U.S. Provisional Patent Application No. 60/471,114, filed May 15, 2003, U.S. Provisional Patent Application No. 60/506,702, filed Sep. 25, 2003, and U.S. Provisional Patent Application No. 60/536,697, filed Jan. 14, 2004.

FIELD OF THE INVENTION

The present invention relates to compositions for delivering peptide YY (PYY) and PYY agonists to a target. These composition include compounds that are well suited for forming non-covalent mixtures with PYY and PYY agonists for administration to animals. Methods for preparation, administration and treatment are also disclosed.

BACKGROUND OF THE INVENTION

Current antiobesity drugs have limited efficacy and numerous side effects. Crowley, V. E., Yeo, G. S. & O'Rahilly, S., *Nat. Rev. Drug Discov* 1, 276-86 (2002). With obesity reaching epidemic proportions worldwide, there is a pressing need for the development of adequate therapeutics in this area. In recent years, hormones and neuropeptides involved in the regulation of appetite, body energy expenditure, and fat mass accumulation have emerged as potential antiobesity drugs. McMinn, J. E., Baskin, D. G. & Schwartz, M. W., *Obes Rev* 1:37-46 (2000), Drazen, D. L. & Woods, S. C., *Curr Opin Clin Nutr Metab Care* 6:621-629 (2003). At present, however, these peptides require parenteral administration. The prospect of daily injections to control obesity is not very encouraging and may limit the use of these drugs.

One such peptide, PYY, is secreted postprandially by endocrine cells of the distal gastrointestinal tract and acts at the hypothalamus signaling satiety. Batterham, R. L. et al., *Nature* 418:650-654 (2002). Recent studies have shown that fasting and postprandial PYY levels are low in obese subjects, which may account for their high appetite and food consumption. When administered intravenously, it suppresses appetite and food intake in both lean and obese subjects. Batterham, R. L. et al., *N Engl J Med* 349:941-948 (2003). Other peptides from the pancreatic peptide (PP) family, like peptide YY fragments (e.g. PYY[3-36]), and PYY agonists (including those not in the PP family) also suppress appetite. Its oral activity, however, is negligible due to its low absorption and rapid degradation in the gastrointestinal tract.

PYY Cancer, Cachexia and Malnutrition: PYY is also secreted by various cancer cells: lung, ovarian, prostate, breast and Barrett's adenocarcinoma, and could act as a marker for or a target for treatment of these other malignancies. Treatment modalities could be directed toward the effects of PYY on cellular apoptosis and/or vascular endothelial growth factor.

PYY has been identified in several carcinoid tumors, and a decreased expression of PYY may be relevant to the development and progression of colon adenocarcinoma. Treatment with PYY decreases growth in pancreatic and breast tumors, most likely through a reduction in intracellular cAMP. Furthermore, PYY has antiproliferative and proapoptotic effects in Barrett's cancer cells. Combined PYY and vitamin E have significant additive antiproliferative effects on breast cancer cell lines regardless of their hormone receptor status. In addition, PYY and vitamin E have growth inhibitory effects on hormone-refractory prostate and pancreatic cancer cells. A biologically active form of vitamin E, alpha-tocopherol succinate (ATS), has been shown to induce apoptosis of hormone-refractory prostate cancer in vitro and inhibit cell growth in vivo.

Taken together, the evidence suggests a potential role for PYY as a therapeutic agent for the treatment or attenuation of multiple cancers.

In cancer patients, PYY may also improve malnutrition that results from iatrogenic causes or cachexia associated with advanced disease. PYY plays a significant role in multiple aspects of cancer from regulation of cell growth to potential therapeutic applications.

PYY and Acute Pancreatitis: Acute pancreatitis (AP) is a disease characterized by inflammation. PYY inhibits NF-k translocation to acinar nuclei in TNF-a-induced AP. Targeted inhibition of transcription factors with PYY may have therapeutic potential in attenuating the progression of pancreatitis.

PYY and Other Gastrointestinal Uses: Because of its slowing effects on gastric motility, PYY has additional potential uses, for example in spastic/irritable bowel, diabetes gastroenteropathy, inflammatory bowel diseases, celiac disease, systemic sclerosis and post-intestinal resection state.

Jean Reubi, Mathias Gugger, Beatrice Waser *Eur J Nucl Med Mol Imaging.* 2002 July; 29(7):855-62. Epub 2002 Apr. 20. Co-expressed peptide receptors in breast cancer as a molecular basis for in vivo multireceptor tumour targeting. Grise K R, Rongione A J, Laird E C, McFadden D W. Peptide YY inhibits growth of human breast cancer in vitro and in vivo. *J Surg Res.* 1999 April; 82(2):151-5. Matsuda K, Maehama T, Kanazawa K. Strumal carcinoid tumor of the ovary: a case exhibiting severe constipation associated with PYY. *Gynecol Oncol.* 2002 October; 87(1):143-5. Yamashita Y, Miyahara E, Shimizu K, Toge T, Adrian T E. Screening of gastrointestinal hormone release in patients with lung cancer. In Vivo. 2003 March-April; 17(2):193-5. Yu A, Somasundar P, Balsubramaniam A, Rose A T, Vona-Davis L, McFadden D W. *J Surg Res.* 2002 Jun. 1; 105(1):65-8. Vitamin E and the Y4 agonist BA-129 decrease prostate cancer growth and production of vascular endothelial growth factor.

At least five distinct neuropeptide Y (NPY) receptors are known to exist, and studies suggest that at least one additional subtype of NPY receptor may exist in rat brains. Dumont, Y., Moyse, E., Fournier, A., Quirion, R., *J. Pharmacol Exp. Ther.*, Jun. 9, 2005; Evidence for the Existence of an Additional Class of Neuropeptide Y Receptor Sites in the Rat Brain.

In the delivery to animals of PYY and PYY agonist, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of PYY and PYY agonist would be the route of choice for administration to animals if not for such biological, chemical, and physical barriers. These agents may be rapidly rendered ineffective or destroyed in the gastro-intestinal tract by acid hydrolysis, enzymes, and the like. In addition, the size and structure of macromolecular drugs may prohibit absorption. As a result, the oral administration of protein and peptide drugs is challenging due, in part, to their low absorption and rapid degradation.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors to inhibit enzymatic degradation. Liposomes have also been described as drug delivery systems for insulin and heparin. However, broad spectrum use of such drug delivery systems is precluded in part because: (1) the systems require toxic amounts of adjuvants or inhibitors; (2) suitable low molecular weight cargos, i.e., active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

According to Batterham et al., *Nature* 418:650-654 (2002), which is hereby incorporated by reference, the peptide YY [3-36] system may provide a therapeutic target for the treatment of obesity.

International Publication No. WO 02/47712 and U.S. Patent Publication No. 2002/0141985 disclose methods for treating obesity and diabetes with peptide YY and peptide YY agonists, such as peptide YY[3-36].

International Publication No. WO 2004/104018 discloses a composition comprising at least one delivery agent compound and at least one of peptide YY (PYY) and a PYY agonist.

There is still a need for simple, inexpensive delivery systems for delivering peptide YY and PYY agonists which are non-invasive and which are convenient, so as to increase patient compliance and acceptability.

SUMMARY OF THE INVENTION

The present invention provides a composition (e.g., a pharmaceutical composition) comprising (a) at least one delivery agent compound and (b) peptide YY (PYY), a PYY agonist, or a mixture thereof. Preferably, the composition includes a therapeutically effective amount of peptide YY and/or the PYY agonist and the delivery agent compound. The composition of the present invention facilitates the delivery of PYY and/or the PYY agonist and increases its bioavailability compared to administration without the delivery agent compound. PYY and PYY agonists possess activity as agents to reduce nutrient availability, including reduction of food intake.

Preferred delivery agent compounds include, but are not limited to, N-(8-[2-hydroxybenzoyl]amino)caprylic acid and N-(10-[2-hydroxybenzoyl]amino)decanoic acid and salts thereof, and solvates and hydrates thereof. In a preferred embodiment, the salt is the sodium salt, such as the monosodium salt.

In one preferred embodiment, the composition comprises peptide YY, a PYY agonist, or a mixture thereof, and at least one delivery agent of the following structure or a salt thereof:

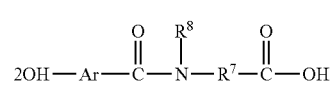

Formula A wherein
Ar is phenyl or naphthyl;
Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;
$R^7$ is selected from $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl($C_1$-$C_{10}$ alkenyl);
$R^8$ is selected from hydrogen, $C_1$ to $C_4$ alkyl, $C_2$ to $C_4$ alkenyl, $C_1$ to $C_4$ alkoxy, and $C_1$-$C_4$ haloalkoxy;
$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, —$CO_2R^9$, or any combination thereof;
$R^9$ is hydrogen, $C_1$ to $C_4$ alkyl, or $C_2$ to $C_4$ alkenyl.
$R^7$ is optionally interrupted by oxygen, nitrogen, sulfur or any combination thereof. In some embodiments, the compounds are not substituted with an amino group in the position alpha to the acid group.

In another preferred embodiment, the composition comprises peptide YY, a PYY agonist, or a mixture thereof, and at least one delivery agent of the following structure or a salt thereof:

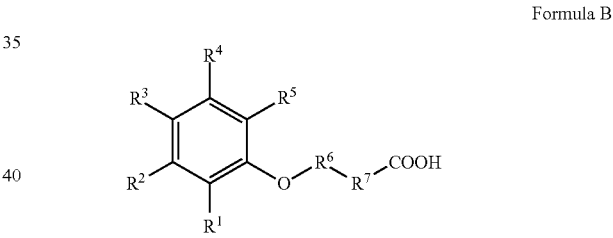

Formula B wherein
$R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}(R^{12})^-$;
$R^5$ is H, —OH, —$NO_2$, halogen, —$CF_3$, —$NR^{14}R^{15}$, —$N^+R^{14}R^{15}R^{16}(R^{13})^-$, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;
$R^5$ is optionally substituted with halogen, —OH, —SH, or —COOH;
$R^5$ is optionally interrupted by O, N, S, or —C(O)—;
$R^6$ is a $C_1$-$C_{12}$ alkylene, $C_2$-$C_{12}$ alkenylene, or arylene;
$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;
$R^6$ is optionally interrupted by O or N;
$R^7$ is a bond or arylene;
$R^7$ is optionally substituted with —OH, halogen, —C(O)$CH_3$, —$NR^{10}R^{11}$, or —$N^+R^{10}R^{11}R^{12}(R^{13})^-$;
each occurrence of $R^8$ is independently H, $C_1$-$C_4$ alkyl, $C_2$-$C_4$ alkenyl, or —$NH_2$;
$R^9$, $R^{10}$, $R^{11}$, and $R^{12}$ independently H or $C_1$-$C_{10}$ alkyl;
$R^{13}$ is a halide, hydroxide, sulfate, tetrafluoroborate, or phosphate;

$R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, or —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —NR$^{14}$R$^{15}$, or N$^+$R$^{14}$R$^{15}$R$^{16}$ ($R^{13}$).

Optionally, when $R^1$, $R^2$, $R^3$, $R^4$, and $R^5$ are H, and $R^7$ is a bond then $R^6$ is not a $C_1$-$C_6$, $C_9$ or $C_{10}$ alkyl.

Optionally, when $R^1$, $R^2$, $R^3$, and $R^4$ are H, $R^5$ is —OH, $R^7$ is a bond then $R^6$ is not a $C_1$-$C_3$ alkyl.

Optionally, when at least one of $R^1$, $R^2$, $R^3$, and $R^4$ is not H, $R^5$ is —OH, $R^7$ is a bond, then $R^6$ is not a $C_1$-$C_4$ alkyl.

Optionally, when $R^1$, $R^2$, and $R^3$ are H, $R^4$ is —OCH$_3$, $R^5$ is —C(O)CH$_3$, and $R^6$ is a bond then $R^7$ is not a $C_3$ alkyl.

Optionally, when $R^1$, $R^2$, $R^4$, and $R^5$ are H, $R^3$ is —OH, and $R^7$ is a bond then $R^6$ is not a methyl.

In yet another embodiment the composition comprises peptide YY, PYY agonist, or a mixture thereof and at least one delivery agent of the following structure or a salt thereof:

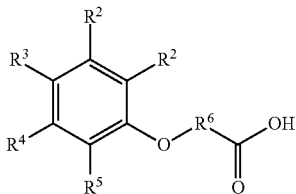

Compound C wherein $R^1$, $R^2$, $R^3$, $R^4$ and $R^5$ are independently H, —CN, —OH, —OCH$_3$, or halogen, at least one of $R^1$, $R^2$, $R^3$, $R^4$ and $R^5$ being —CN; and $R^6$ is a $C_1$-$C_{12}$ linear or branched alkylene, alkenylene, arylene, alkyl(arylene) or aryl(alkylene).

According to one embodiment, when $R^1$ is —CN, $R^4$ is H or —CN, and $R^2$, $R^3$, and $R^5$ are H, then $R^6$ is not methylene (CH$_2$)$_1$).

Also provided is a dosage unit form (e.g., an oral or buccal dosage unit form) comprising the composition of the present invention. The dosage unit form may be in the form of a liquid or a solid, such as a tablet, capsule or particle, including a powder or sachet.

Another embodiment is a method for administering peptide YY, a PYY agonist, or a mixture thereof to an animal in need thereof, by administering the composition or dosage unit form(s) of the present invention to the animal. The preferred route of administration is oral or buccal.

Another embodiment is a method for administering peptide YY, a PYY agonist, or a mixture thereof to an animal in need thereof, by administering the composition or dosage unit form(s) of the present invention to the animal in a manner to minimize or prevent formation of antibodies to the peptide YY and/or a PYY agonist.

Yet another embodiment is a method of losing weight in an animal (such as a human) in need thereof by administering an effective amount of the composition or dosage unit form(s) of the present invention to the animal. In other words, an effective amount of the delivery agent compound to facilitate the delivery of the PYY or PYY agonist and an effective amount (e.g., a therapeutically effective amount) of PYY or PYY agonist are administered.

Yet another embodiment is a method of treating obesity in an animal (such as a human) in need thereof by administering an effective amount of the composition of the present invention to the animal.

Yet another embodiment is a method for treating conditions or disorders which can be alleviated by reducing nutrient availability in an animal (such as a human) by administering to the animal a therapeutically effective amount of the composition or dosage unit form(s) of the present invention. Such conditions and disorders, include but are not limited to, hypertension, dyslipidemia, cardiovascular risk, an eating disorder, insulin-resistance, obesity, and diabetes mellitus.

Yet another embodiment is a method of improving the lipid profile in an animal (such as a human) by administering to the animal an effective amount of the composition or dosage unit form(s) of the present invention.

Yet another embodiment is a method of preparing a composition of the present invention by mixing at least one delivery agent compound and at least one of peptide YY and a PYY agonist.

Yet another embodiment is a dosage unit form for buccal administration comprising at least one delivery agent compound and at least one of peptide YY and a PYY agonist. The dosage unit form may be, for example, in the form of a solid, such as a tablet or candy which dissolves in the mouth, a powder, a liquid, or a thin sheet, or any other form which dissolves and/or sticks to the interior of the mouth, or facilitates the buccal administration of PYY or PYY agonist.

Another embodiment is a method for buccally administering peptide YY, a PYY agonist, or a mixture thereof to an animal in need thereof, by buccally administering the composition or dosage unit form(s) of the present invention to the animal. Preferably, it is administered in a manner to minimize or prevent formation of antibodies to the peptide YY and/or a PYY agonist.

Yet another embodiment is a method for treating conditions or disorders which can be alleviated by reducing nutrient availability in an animal (such as a human) by buccally administering to the animal a therapeutically effective amount of the composition or dosage unit form(s) of the present invention. Such conditions and disorders, include but are not limited to, those described above.

Yet another embodiment is a method of losing weight in an animal (such as a human) in need thereof by buccally administering an effective amount of the composition or dosage unit form(s) of the present invention to the animal.

Yet another embodiment is a method of treating obesity in an animal (such as a human) in need thereof by buccally administering an effective amount of the composition of the present invention to the animal.

Yet another embodiment is a method of improving the lipid profile in an animal (such as a human) by buccally administering to the animal an effective amount of the composition or dosage unit form(s) of the present invention.

Yet another embodiment is a method of treating or attenuating one or more cancers in an animal (such as a human) by buccally administering an effective amount of the composition of the present invention to the animal.

BRIEF DESCRIPTION OF THE DRAWINGS

FIG. 1 is a graph of serum PYY concentrations in beagles versus time after buccal administration of 0.1 mg/kg of PYY and 10 mg/kg of SNAD.

DETAILED DESCRIPTION OF THE INVENTION

Embodiments of the invention may comprise dosage unit forms for buccal administration comprising (a) at least one peptide YY, a peptide YY agonist, or a mixture thereof, and (b) a delivery agent of the formula

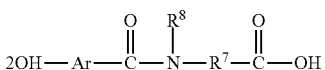

or a salt thereof, wherein:

Ar is phenyl or naphthyl;

Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;

$R^7$ is selected from $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl($C_1$-$C_{10}$ alkenyl);

$R^8$ is selected from hydrogen, $C_1$ to $C_4$ alkyl, $C_2$ to $C_4$ alkenyl, $C_1$ to $C_4$ alkoxy, and $C_1$-$C_4$ haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —$CO_2R^9$, or any combination thereof;

$R^9$ is hydrogen, $C_1$ to $C_4$ alkyl, or $C_2$ to $C_4$ alkenyl; and $R^7$ is optionally interrupted by oxygen, nitrogen, sulfur or any combination thereof. In some embodiments, the compounds are not substituted with an amino group in the position alpha to the acid group.

Embodiments of the invention may comprise dosage unit forms for buccal administration comprising (a) at least one peptide YY, a peptide YY agonist, or a mixture thereof, and (b) a delivery agent of the formula

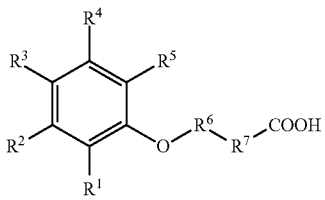

or a salt thereof, wherein $R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)$R^8$, —$NO_2$, —$NR^9R^{10}$, or —$N^+R^9R^{10}R^{11}$ ($R^{12}$)⁻;

$R^5$ is H, —OH, —$NO_2$, halogen, —$CF_3$, —$NR^{14}R^{15}$, —$N^+R^{14}R^{15}R^{16}$ ($R^{13}$)⁻, amide, $C_1$-$C_{12}$ alkoxy, $C_1$-$C_{12}$ alkyl, $C_2$-$C_{12}$ alkenyl, carbamate, carbonate, urea, or —C(O)$R^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —$NH_2$, or —$CO_2R^8$;

$R^6$ is optionally interrupted by O or N;

$R^7$ is a bond or arylene;

$R^7$ is optionally substituted with —OH, halogen, —C(O)$CH_3$, —$NR^{10}R^{11}$, or —$N^+R^{10}R^{11}R^{12}(R^{13})^-$;

$R^8$ is H, $C_1$-$C_4$ alkyl, $C_2$-$C_4$ alkenyl, or —$NH_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)$R^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —$NR^{14}R^{15}$, or $N^+R^{14}R^{15}R^{16}$ ($R^{13}$).

Embodiments of the invention may comprise dosage unit forms for buccal administration comprising (a) at least one peptide YY, a peptide YY agonist, or a mixture thereof, and (b) a delivery agent of the formula

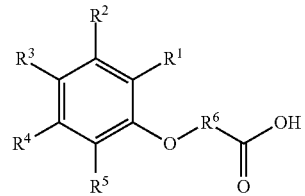

or a salt thereof, wherein $R^1$, $R^2$, $R^3$, $R^4$ and $R^5$ are independently H, —CN, —OH, —$OCH_3$, or halogen, at least one of $R^1$, $R^2$, $R^3$, $R^4$ and $R^5$ being —CN; and $R^6$ is $C_1$-$C_{12}$ linear or branched alkylene, alkenylene, arylene, alkyl(arylene) or aryl(alkylene).

Embodiments of the invention may comprise a delivery agent selected from the group comprising the monosodium salt of N-(8-[2-hydroxybenzoyl]-amino)caprylic acid, the monosodium salt of N-(10-[2-hydroxybenzoyl]-amino)decanoic acid, the monosodium salt of 8-(2-hydroxy-4-methoxybenzoylamino)octanoic acid, the monosodium salt of 8-(2,6-dihydroxybenzoylamino)octanoic acid, the monosodium salt of 8-(2-hydroxy-5-bromobenzoylamino)octanoic acid, the monosodium salt 8-(2-hydroxy-5-chlorobenzoylamino)octanoic acid, the monosodium salt of 8-(2-hydroxy-5-iodobenzoylamino)octanoic acid, the monosodium salt of 8-(2-hydroxy-5-methylbenzoylamino)octanoic acid, the monosodium salt of 8-(2-hydroxy-5-fluorobenzoylamino) octanoic acid, the monosodium salt of 8-(2-hydroxy-5-methoxybenzoylamino)octanoic acid, the monosodium salt of 8-(3-hydroxyphenoxy)octanoic acid, the monosodium salt of 8-(4-hydroxyphenoxy)octanoic acid, the monosodium salt of 6-(2-cyanophenoxy)hexanoic acid, the monosodium salt of 8-(2-Hydroxyphenoxy)octyl-diethanolamine, disodium salt of N-(10-[2-hydroxybenzoyl]-amino)decanoic acid, the disodium salt of 8-(4-hydroxyphenoxy)octanoate, the monosodium salt of 8-(4-hydroxyphenoxy)octanoate, the disodium salt of 8-(2-hydroxy-4-methoxybenzoylamino)octanoic acid, and the disodium salt of 8-(2-hydroxy-5-methoxybenzoylamino)octanoic acid.

Embodiments of the invention may comprise a delivery agent N-(8-[2-hydroxybenzoyl]-amino)caprylic acid or a pharmaceutically acceptable salt thereof, or N-(10-[2-hydroxybenzoyl]-amino)decanoic acid or a pharmaceutically acceptable salt thereof.

Embodiments of the invention may comprise a peptide YY agonist selected from the functional domain of PYY, active fragments of PYY, derivatives of PYY, fragments of PYY, or analogs of PYY. The peptide YY agonist may, e.g., be PYY [3-36].

Embodiments of the invention may comprise any dosage unit form described above with an excipient, a diluent, a disintegrant, a lubricant, a plasticizer, a colorant, a dosing vehicle, or any combination thereof.

Embodiments of the invention may comprise dosage unit forms in the form of, e.g., a tablet, a capsule, a particle, a powder, a sachet, or a liquid.

Embodiments of the invention may comprise a dosing vehicle which is a liquid selected from the group comprising, e.g., water, aqueous propylene glycol, phosphate buffer, 1,2-propane diol, ethanol, or any combination thereof.

Embodiments of the invention may comprise methods for administering an effective amount of peptide YY, a peptide YY agonist or a combination thereof, to a patient in need thereof, comprising the step of buccally administering any of the dosage unit forms described above. The peptide YY agonist may be, e.g., PYY[3-36] and the delivery agent may be, e.g., N-(8-[2-hydroxybenzoyl]-amino)caprylic acid or N-(10-[2-hydroxybenzoyl]-amino)decanoic acid or a pharmaceutically acceptable salt thereof.

Embodiments of the invention may comprise methods of treating obesity in a patient in need thereof, comprising the step of administering to the patient an effective amount of any of the dosage unit forms described above.

Embodiments of the invention may comprise methods of treating a condition or disorder that may be alleviated by reducing nutrient availability in a patient in need thereof, comprising the step of administering to an animal an effective amount of any of the dosage unit forms described above. The condition or disorder may, e.g., be selected from the group comprising hypertension, dyslipidemia, cardiovascular risk, an eating disorder, insulin-resistance, obesity diabetes mellitus, cancer, cachexia and malnutrition, or any combination thereof.

Embodiments of the invention may comprise methods of reducing nutrient uptake in a patient in need thereof, comprising the step of administering an effective amount of any of the dosage unit forms described above.

Embodiments of the invention may comprise methods of improving the lipid profile in a patient in need thereof, comprising the step of administering an effective amount of any of the dosage unit forms described above.

Embodiments of the invention may comprise methods of improving the bioavailability of peptide YY or a peptide YY agonist in an animal, the method comprising the step of administering any of the dosage unit forms described above.

Embodiments of the invention may comprise methods of preparing a dosage unit form comprising the step of mixing at least one of a peptide YY and a peptide YY agonist, and a delivery agent of the formula

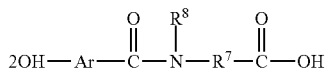

or a salt thereof, wherein:

Ar is phenyl or naphthyl;

Ar is optionally substituted with one or more of —OH, halogen, $C_1$-$C_4$ alkyl, $C_1$-$C_4$ alkenyl, $C_1$-$C_4$ alkoxy or $C_1$-$C_4$ haloalkoxy;

$R^7$ is selected from $C_4$-$C_{20}$ alkyl, $C_4$-$C_{20}$ alkenyl, phenyl, naphthyl, ($C_1$-$C_{10}$ alkyl)phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl($C_1$-$C_{10}$ alkenyl);

$R^8$ is selected from hydrogen, $C_1$ to $C_4$ alkyl, $C_2$ to $C_4$ alkenyl, $C_1$ to $C_4$ alkoxy, and $C_1$-$C_4$ haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —$CO_2R^9$, or any combination thereof;

$R^9$ is hydrogen, $C_1$ to $C_4$ alkyl, or $C_2$ to $C_4$ alkenyl; and $R^7$ is optionally interrupted by oxygen, nitrogen, sulfur or any combination thereof.

DEFINITIONS

The term "hydrate" as used herein includes, but is not limited to, (i) a substance containing water combined in the molecular form and (ii) a crystalline substance containing one or more molecules of water of crystallization or a crystalline material containing free water.

The term "solvate" as used herein includes, but is not limited to, a molecular or ionic complex of molecules or ions of a solvent with molecules or ions of the delivery agent compound or salt thereof, or hydrate or solvate thereof.

The term "delivery agent" refers to any of the delivery agent compounds disclosed herein.

The term "SNAC" refers to the monosodium salt of N-(8-[2-hydroxybenzoyl]-amino)caprylic acid.

The term "SNAD" refers to the monosodium salt of N-(10-[2-hydroxybenzoyl]-amino)decanoic acid. The term "disodium salt of SNAD" refers to the disodium salt of N-(10-[2-hydroxybenzoyl]-aminodecanoic acid.

An "effective amount of PYY, PYY agonist, or a mixture thereof" is an amount of the PYY, the PYY agonist, or mixture thereof which is effective to treat or prevent a condition in a living organism to whom it is administered over some period of time, e.g., provides a therapeutic effect during a desired dosing interval.

An "effective amount of delivery agent" is an amount of the delivery agent which enables and/or facilitates the absorption of a desired amount of PYY or PYY agonist via any route of administration (such as those discussed in this application including, but not limited to, the oral (e.g., across a biological membrane in the gastrointestinal tract), nasal, pulmonary, dermal, buccal, vaginal, and/or ocular route).

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak) represents the arithmetic mean value of the pharmacokinetic value unless otherwise specified.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "about" generally means within 10%, preferably within 5%, and more preferably within 1% of a given value or range.

The terms "alkyl" and "alkenyl" as used herein include linear and branched alkyl and alkenyl substituents, respectively.

The term "patient" as used herein refers to a mammal and preferably a human.

The phrase "pharmaceutically acceptable" refers to additives or compositions that are physiologically tolerable when administered to a mammal.

The terms "buccal administration" and "buccally administering" include administration by adsorption through any surface inside the mouth or upper throat (such as the cheek (e.g., the inner cheek lining), gums, palate, tongue, tonsils, periodontal tissue, lips, and the mucosa of the mouth and pharynx). These terms, for example, include sublingual and intraoral administration.

PYY and PYY Agonists

By "peptide YY" or "PYY" is meant a Peptide YY polypeptide obtained or derived from any species. Thus, the term "PYY" includes both the human full length, 36 amino acid peptide as set forth in SEQ ID NO: 2 of International Publication No. WO 02/47712 (which is the PCT counterpart to U.S. Patent Publication No. 2002/0141985, which is hereby incorporated by reference) (SEQ ID NO: 1) and Tatemoto, Proc Natl Acad Sci U.S.A. 79:2514-8, 1982, and species variations of PYY, including e.g., murine, hamster, chicken, bovine, rat, and dog PYY, for example. By "PYY agonist" is meant any compound which elicits an effect of PYY to reduce nutrient availability, for example a compound (1) having activity in the food intake, gastric emptying, pancreatic secretion, or weight loss assays described in Examples 1, 2, 5, or 6 of WO 02/47712 and U.S. Patent Publication No. 2002/0141985, and (2) which binds specifically in a Y receptor assay (Example 10 of WO 02/47712 and U.S. Patent Publication No. 2002/0141985) or in a competitive binding assay with labeled PYY or PYY [3-36] from certain tissues having an abundance of Y receptors, including e.g., area postrema (Example 9 of WO 02/47712 and U.S. Patent Publication No. 2002/0141985), wherein the PYY agonist is not pancreatic polypeptide. Preferably, PYY agonists would bind in such assays with an affinity of greater than about 1 µM, and more preferably with an affinity of greater than about 1 to about 5 nM.

Such agonists can comprise a polypeptide having a functional PYY domain, an active fragment of PYY, or a chemical or small molecule. PYY agonists may be peptide or nonpeptide compounds, and include "PYY agonist analogs," which refer to any compound structurally similar to a PYY that have PYY activity typically by virtue of binding to or otherwise directly or indirectly interacting with a PYY receptor or other receptor or receptors with which PYY itself may interact to elicit a biological response. Such compounds include derivatives of PYY, fragments of PYY, extended PYY molecules having more than 36 amino acids, truncated PYY molecules having less than 36 amino acids, and substituted PYY molecules having one or more different amino acids, or any combination of the above. Such compounds may also be modified by processes such as pegylation, amidation, glycosylation, acylation, sulfation, phosphorylation, acetylation and cyclization.

One such PYY agonist analog is PYY [3-36], identified as SEQ ID NO: 3 of WO 02/47712 and U.S. Patent Publication No. 2002/0141985 (SEQ ID NO: 2); Eberlein, Eysselein et al., Peptides 10:797-803 (1989); and Grandy, Schimiczek et al, Regul Pept 51:151-9 (1994). Polypeptides with numbers in brackets refer to truncated polypeptides having the sequence of the full length peptide over the amino acid positions in the brackets. Thus, PYY [3-36] has a sequence identical to PYY over amino acids 3 to 36. PYY[3-36] contains approximately 40% of total peptide YY-like immunoreactivity in human and canine intestinal extracts and about 36% of total plasma peptide YY immunoreactivity in a fasting state to slightly over 50% following a meal. It is apparently a dipeptidyl peptidase-IV (DPP4) cleavage product of peptide YY. Peptide YY[3-36] is reportedly a selective ligand at the Y2 and Y5 receptors, which appear pharmacologically unique in preferring N-terminally truncated (i.e. C terminal fragments of) neuropeptide Y analogs. A PYY agonist may bind to a PYY receptor with higher or lower affinity, demonstrate a longer or shorter half-life in vivo or in vitro, or be more or less effective than native PYY.

Other suitable PYY agonists include those described in International Publication No. WO 98/20885, which is hereby incorporated by reference.

By "condition or disorder which can be alleviated by reducing caloric (or nutrient) availability" is meant any condition or disorder in an animal that is either caused by, complicated by, or aggravated by a relatively high nutrient availability, or that can be alleviated by reducing nutrient availability, for example by decreasing food intake. Such conditions or disorders include, but are not limited to, obesity, diabetes, including type 2 diabetes, eating disorders, and insulin-resistance syndromes.

In one aspect, the invention provides a method of treating obesity in an obese or overweight animal by administering a therapeutically effective amount of PYY, a PYY agonist, or a mixture thereof with at least one delivery agent compound. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method.

In other aspects, the invention features methods of reducing food intake, treating diabetes mellitus, and improving lipid profile (including reducing LDL, HDL, VLDL, total cholesterol and/or triglyceride levels) comprising administering to a subject a therapeutically effective amount of PYY, a PYY agonist, or a mixture thereof with at least one delivery agent compound. In a preferred embodiment, the methods of the invention are used to treat conditions or disorders which can be alleviated by reducing nutrient availability in a subject in need thereof, comprising administering to said subject a therapeutically effective amount of PYY, a PYY agonist, or a mixture thereof with at least one delivery agent compound. Such conditions and disorders include, but are not limited to, hypertension, dyslipidemia, cardiovascular disease, eating disorders, insulin-resistance, obesity, and diabetes mellitus of any kind.

In the methods of the invention, preferred PYY agonists are those having a potency in one of the assays described in WO 02/47712 and U.S. Patent Publication No. 2002/0141985 (preferably food intake, gastric emptying, pancreatic secretion, or weight reduction assays) which is greater than the potency of NPY (Neuropeptide Y) in that same assay.

In one embodiment, for treatment of all conditions and disorders described herein, a preferred PYY agonist is PYY [3-36], and is administered (e.g. peripherally) at a dose of about 1 pg to about 5 mg per day in single or divided doses. Alternatively PYY[3-36] may be administered on the basis of the recipients total body weight in an amount of about 0.01 µg/kg to about 500 µg/kg, or about 0.05 µg/kg to about 250 µg/kg, or less than about 50 µg/kg, per day in a single or divided doses. Dosages in these ranges will vary with the potency of each agonist, of course, and are readily determined by one of skill in the art.

In the methods of the present invention, PYY's and PYY agonists with the delivery agent compound may be administered separately or together with one or more other compounds and compositions that exhibit a long term or short-term action to reduce nutrient availability, including, but not limited to other compounds and compositions that comprise an amylin or amylin agonist, a cholecystokinin (CCK) or CCK agonist, a leptin (OB protein) or leptin agonist, an exendin or exendin agonist, or a GLP-1 or GLP-1 agonist. Suitable amylin agonists include, for example, [25,28, 29Pro-]-human amylin (also known as "pramlintide", and described in U.S. Pat. Nos. 5,686,511 and 5,998,367), calcitonin (e.g., salmon calcitonin), including those described in U.S. Pat. No. 5,739,106, which is hereby incorporated by reference. The CCK used is preferably CCK octopeptide (CCK-8). Leptin is discussed in, for example, Pelleymounter, C. et al., Science 269: 540-543 (1995), Halaas, G. et al., Science 269: 543-6 (1995) and Campfield, S. et al., Science 269: 546-549 (1995). Suitable CCK agonist includes those described in U.S. Pat. No. 5,739,106, which is hereby incorporated by reference. Suitable exendins include exendin-3 and exendin-4, and exendin agonist compounds include, for example, those described in PCT Publications WO 99/07404, WO 99/25727, and WO 99/25728, all of which are hereby incorporated by reference. According to one embodiment, the composition of the present invention includes at least one delivery agent compound, PYY, a PYY agonist, or a mixture thereof, at least one amylin agonist, and a CCK agonist. Suitable combinations of amylin agonist and CCK agonist include, but are not limited to, those described in U.S. Pat. No. 5,739,106, which is hereby incorporated by reference.

PYY and PYY[3-36] are C-terminally amidated when expressed physiologically, but need not be for the purposes of the present invention. These peptides may also have other posttranslational modifications.

PYY and peptide-based PYY agonists described herein may be prepared using standard recombinant expression or chemical peptide synthesis techniques known in the art, e.g., using an automated or semiautomated peptide synthesizer. PYY as described herein include any morphologies of PYY [3-36], including those obtained by lyophilization, crystallization, reconstitution, spray drying, and super critical fluid processing.

Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, 6: 4970, Applied Biosystems, Inc., Foster City, Calif.) with capping. Peptides may be also be assembled using an Advanced Chem Tech Synthesizer (Model MPS 350, Louisville, Ky.). Peptides may be purified by RP-HPLC (preparative and analytical) using, e.g., a Waters Delta Prep 3000 system and a C4, C8 or C18 preparative column (10p, 2.2×25 cm; Vydac, Hesperia, Calif.).

Peptide compounds useful in the invention may also be prepared using recombinant DNA techniques, using methods now known in the art. See, e.g., Sambrook et al., Molecular Cloning: A Laboratory Manual, 2d Ed., Cold Spring Harbor (1989). Non-peptide compounds useful in the present invention may be prepared by art-known methods. For example, phosphate-containing amino acids and peptides containing such amino acids, may be prepared using methods known in the art. See, e.g., Bartlett and Landen, Biorg Chem. 14: 356-377 (1986).

The compositions useful in the invention can be provided as parenteral compositions for e.g., injection or infusion. For example, they may be suspended in an aqueous carrier, for example, in an isotonic buffer solution at a pH of about 3.0 to about 8.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

Since PYY and many PYY agonists are amphoteric, they may be utilized as free bases, as acid addition salts or as metal salts. The salts preferably are pharmaceutically acceptable, and these will include metal salts, particularly alkali and alkaline earth metal salts, e.g., potassium or sodium salts. A wide variety of pharmaceutically acceptable acid addition salts are available. Such products are readily prepared by procedures well known to those skilled in the art.

Therapeutically effective amounts of a PYY or a PYY agonist for use in reducing nutrient availability are those that suppress appetite at a desired level. As will be recognized by those in the field, an effective amount of therapeutic agent will vary with many factors including the age and weight of the patient, the patient's physical condition, the blood sugar level, the weight level to be obtained, and other factors.

The effective daily appetite-suppressing dose of PYY, a PYY agonist, or a mixture thereof may be in the range of about 1 to 30 µg to about 50 mg/day, or about 10 to 30 µg to about 20 mg/day and or about 5 to 100 µg to about 10 mg/day, or about 5 µg to about 5 mg/day, for a 50 kg patient. Effective amounts of PYY or a PYY agonist may be administered in a single or divided doses. The dosages may be between about 0.01 to about 1 mg/kg/dose. The exact dose to be administered may be determined by one of skill in the art and is dependent upon the potency of PYY, PYY agonist, or mixture thereof, as well as upon the age, weight and condition of the individual. Administration should begin whenever the suppression of nutrient availability, food intake, weight, blood glucose or plasma lipid lowering is desired, for example, at the first sign of symptoms or shortly after diagnosis of obesity, diabetes mellitus, or insulin resistance syndrome.

Screening for Additional PYY Agonists

Other PYY agonists can be identified by using the receptor binding assays described below (e.g., in Examples 9 and 10 of WO 02/47712 and U.S. Patent Publication No. 2002/0141985) or known in the art in combination with the physiological screens described in the examples in WO 02/47712 and U.S. Patent Publication No. 2002/0141985. Potential PYY agonists can be compared with the activity of PYY or PYY [3-36].

Alternatively, once one or more PYY-preferring (Y7) receptors have been characterized and cloned, alternative assays and high throughput screens can be implemented as discussed below or known in the art. Y7 receptors are those with an affinity for PYY or PYY [3-36] greater than their affinity for neuropeptide Y (NPY). Methods of screening for compounds which modulate PYY receptor activity comprise contacting test compounds with PYY receptors and assaying for the presence of a complex between the compound and the PYY receptors. In such assays, the test ligand is typically labeled. After suitable incubation, free ligand is separated from that present in bound form, and the amount of free or uncomplexed label is a measure of the ability of the particular compound to bind to the PYY receptors.

Alternatively, bound labeled ligand may be measured (e.g., using expressed membrane bound Y7 receptors).

High throughput screening for PYY agonists having suitable binding affinity to PYY receptors may be employed. For example, large numbers of different small peptide test compounds are synthesized on a solid substrate. The peptide test compounds are contacted with the PYY receptor and washed. Bound PYY receptor is then detected by methods well known in the art. Purified test compounds can also be coated directly onto plates for use in the aforementioned drug screening techniques. In addition, if the test compounds are proteins, antibodies can be used to capture the protein and immobilize it on the solid support by any means known in the art.

Competitive screening assays may be used in which neutralizing antibodies capable of binding a polypeptide of the invention specifically compete with a test compound for binding to the polypeptide. In this manner, the antibodies can be used to detect the presence of any peptide that shares one or more antigenic determinants with a PYY agonist. Radiolabeled competitive binding studies are described in Lin, A. H.

et al., *Antimicrobial Agents and Chemotherapy* 41(10): 2127-2131 (1997), the disclosure of which is incorporated herein by reference in its entirety.

Delivery Agent Compounds

The delivery agent compound may be any of those described in U.S. Pat. Nos. 5,650,386 and 5,866,536 and International Publication Nos. WO94/23767, WO95/11690, WO95/28920, WO95/28838, WO96/10396, WO96/09813, WO96/12473, WO96/12475, WO96/30036, WO96/33699, WO97/31938, WO97/36480, WO98/21951, WO98/25589, WO98/34632, WO98/49135, WO99/16427, WO00/06534, WO00/07979, WO00/40203, WO00/46182, WO00/47188, WO00/48589, WO00/50386, WO00/59863, WO00/59480, WO01/32130, WO01/32596, WO01/34114, WO01/44199, WO01/51454, WO01/70219, WO01/92206, WO02/02509, WO02/15959, WO02/16309, WO02/20466, WO02/19969, WO02/070438, WO03/026582, WO02/100338, WO03/045306, and WO0326582, all of which are hereby incorporated by reference.

Non-limiting examples of delivery agent compounds include N-(8-[2-hydroxybenzoyl]-amino)caprylic acid, N-(10-[2-hydroxybenzoyl]-amino)decanoic acid, 8-(2-hydroxy-4-methoxybenzoylamino)octanoic acid, 8-(2,6-dihydroxybenzoylamino)octanoic acid, 8-(2-hydroxy-5-bromobenzoylamino)octanoic acid, 8-(2-hydroxy-5-chlorobenzoylamino)octanoic acid, 8-(2-hydroxy-5-iodobenzoylamino)octanoic acid, 8-(2-hydroxy-5-methylbenzoylamino)octanoic acid, 8-(2-hydroxy-5-fluorobenzoylamino)octanoic acid, 8-(2-hydroxy-5-methoxybenzoylamino)octanoic acid, 8-(3-hydroxyphenoxy)octanoic acid, 8-(4-hydroxyphenoxy) octanoic acid, 6-(2-cyanophenoxy)hexanoic acid, 8-(2-Hydroxyphenoxy)octyl-diethanolamine, 8-(4-hydroxyphenoxy)octanoate, 8-(4-hydroxyphenoxy) octanoate, 8-(2-hydroxy-4-methoxybenzoylamino)octanoic acid, 8-(2-hydroxy-5-methoxybenzoylamino)-octanoic acid., and salts thereof. Preferred salts include, but are not limited to, monosodium and disodium salts.

The delivery agent compounds may be in the form of the carboxylic acid or pharmaceutically acceptable salts thereof, such as sodium salts, and hydrates and solvates thereof. The salts may be mono- or multi-valent salts, such as monosodium salts and disodium salts. The delivery agent compounds may contain different counter ions chosen for example due to their effect on modifying the dissolution profile of the carrier.

The delivery agent compounds may be prepared by methods known in the art, such as those discussed in the aforementioned publications (e.g., International Publication Nos. WO 98/34632, WO 00/07979, WO 01/44199, WO 01/32596, WO 02/20466, and WO 03/045306). SNAC, SNAD, and the free acid and other salts thereof may be prepared by any method known in the art, such as those described in U.S. Pat. Nos. 5,650,386 and 5,866,536.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Delivery Systems

The composition of the present invention comprises one or more delivery agent compounds of the present invention and/or one or more of PYY and PYY agonists. The delivery agent compound and PYY and/or the PYY agonists are typically mixed prior to administration to form an administration composition.

The composition may include one or more food-intake-reducing, plasma glucose-lowering or plasma lipid-altering agents, such as an amylin, an amylin agonist, a CCK, or CCK agonist, or a leptin or leptin agonist, or an exendin or exendin agonist.

The administration compositions may be in the form of a liquid. The solution medium may comprise dosing vehicles such as, e.g., water, 25% aqueous propylene glycol, or phosphate buffer. Other dosing vehicles include polyethylene glycol. Dosing solutions may be prepared by mixing a solution of the delivery agent compound with a solution of the active agent, just prior to administration. Alternately, a solution of the delivery agent compound (or PYY, PYY agonist, or mixture thereof) may be mixed with the solid form of PYY or the PYY agonist (or delivery agent compound). The delivery agent compound and PYY, PYY agonist, or mixture thereof may also be mixed as dry powders. The delivery agent compound and PYY, PYY agonist, or mixture thereof can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of PYY, PYY agonist, or mixture thereof. Alternately, a solid may be obtained from a solution of compound and PYY, PYY agonist, or mixture thereof by methods known in the art, such as freeze-drying (lyophilization), precipitation, crystallization and solid dispersion. Alternatively, the administration can be a semi-solid, in the form of a gel, paste, colloid, gelatin, emulsion, suspension and the like.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (TRASYOL®) and Bowman-Birk inhibitor.

The amount of PYY and/or the PYY agonist used in an administration composition of the present invention is an amount effective to treat the target indication. However, the amount can be less than that amount when the composition is used in a dosage unit form because the dosage unit form may contain a plurality of delivery agent compound/PYY or the PYY agonist compositions or may contain a divided effective amount. The total effective amount can then be administered in cumulative units containing, in total, an effective amount of PYY, PYY agonist, or mixture thereof. Moreover, those skilled in the filed will recognize that an effective amount of PYY, PYY agonist, or mixture thereof will vary with many factors including the age and weight of the patient, the patient's physical condition, the blood sugar level, the weight level to be obtained, as well as other factors.

The total amount to be used of PYY or the PYY agonist can be determined by methods known to those skilled in the art. However, because the compositions of the invention may deliver PYY or the PYY agonist more efficiently than compositions containing PYY or the PYY agonist alone, lower amounts of PYY or the PYY agonist than those used in prior dosage unit forms or delivery systems can be administered to the subject, while still achieving the same blood levels and/or therapeutic effects.

According to one embodiment the amount of PYY, PYY agonist, or mixture thereof administered with the delivery agent is an amount sufficient to suppress appetite to a desired level. The effective daily appetite-suppressing dose of PYY, a PYY agonist, or a mixture thereof generally ranges from about 1 µg about 5 mg per day in single or divided doses, preferably from about 5 µg to about 2 mg/day, and more preferably from about 5 µg to 500 µg/day for a 50 kg patient. Preferably the dosage forms of the present invention consist from about 0.01 and about 10 µg/kg/dose of PYY, a PYY agonist, or a mixture thereof.

The present invention also includes pharmaceutical compositions and dosage forms which include the aforementioned amounts of PYY, a PYY agonist, or a mixture thereof and at least one delivery agent Generally an effective amount of delivery agent to facilitate the delivery of PYY and/or the PYY agonist is administered with PYY, PYY agonist, or a mixture thereof. Generally the amount of delivery agent to PYY, PYY agonist, or mixture thereof, on a molar basis ranges from about 25000:1 to about 50:1, preferably from about 8000:1 to about 100:1 and most preferably from about 4000:1 to about 300:1. It is envisioned that ratios smaller than about 50:1, possibly as small as about 1:1, or less than about 1:1, may be efficacious in some circumstances.

The presently disclosed delivery agent compounds facilitate the delivery of PYY, a PYY agonist, or a mixture thereof, particularly in oral, intranasal, sublingual, intraduodenal, subcutaneous, buccal, intracolonic, rectal, vaginal, mucosal, pulmonary, transdermal, intradermal, parenteral, intraperitoneal, intravenous, intramuscular and ocular systems, as well as traversing the blood-brain barrier. The compositions and dosage unit forms of the present invention may be administered by any of the aforementioned routes.

The compositions and dosage unit form of the present invention when administered orally or buccally to a human may achieve known therapeutic levels of PYY[3-36] in the body, such as those enumerated in Batterham et al., *Nature* 418:650-654 (2002).

Without being bound by any particular theory, applicants believe that the compositions of the present invention may be administered buccally, and that there is less dilution and fewer food effects when PYY or PYY agonist is absorbed buccally. Buccal administration can also provide a sustained (flat) release profile, which is helpful, for example, to prevent subjects from eating over a longer time period.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

Dosage unit forms for buccal administrations may contain ingredients known to facilitate buccal administration. The buccal dosage unit form, for example, may be formulated so as to erode gradually over a predetermined time period and release the PYY or PYY agonist and delivery agent at a constant or substantially constant rate. According to one embodiment, the time period ranges from about 0.5 hours to about 24 hours. A bioerodible (hydrolyzable) polymeric carrier that adheres the dosage form to the buccal mucosa, such as that described in U.S. Published Patent Application No. 2003/0134861 (which is hereby incorporated by reference), can be used, e.g., to provide a sustained release profile. Suitable bioerodible (hydrolyzable) polymeric carriers include, but are not limited to, those which provide a sustained release profile and are compatible with the PYY or PYY agonist and delivery agent. According to one embodiment, the polymeric carrier comprises hydrophilic (water-soluble and water-swellable) polymers that adhere to the wet surface of the buccal mucosa. Non-limiting examples of polymeric carriers useful herein include acrylic acid polymers, e.g., those known as "carbomers" (CARBOPOL®, which may be obtained from B. F. Goodrich is one such polymer). Other suitable polymers include, but are not limited to: hydrolyzed polyvinylalcohol; polyethylene oxides (e.g., SENTRY POLOX® water soluble resins, available from Union Carbide of Midland, Mich.); polyacrylates (e.g., GANTREZ®, which may be obtained from GAF of Wayne, N.J.); vinyl polymers and copolymers; polyvinylpyrrolidone; dextran; guar gum; pectins; starches; and cellulosic polymers such as hydroxypropyl methylcellulose (e.g., METHOCEL®, which may be obtained from the Dow Chemical Company of Midland, Mich.), hydroxypropyl cellulose (e.g., KLUCEL®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Non-limiting examples of disintegrants are manitol, sodium starch gyycolate, cross-linked polyvinylpyrrolidones, such as crospovidone (e.g., POLYPLASDONE® XL, which may be obtained from GAF), cross-linked carboxylic methylcelluloses, such as croscarmelose (e.g., AC-DI-SOL®, which may be obtained from FMC Corporation of Philadelphia, Pa.), alginic acid, and sodium carboxymethyl starches (e.g., EXPLOTAB®, which may be obtained from Edward Medell Co., Inc.), methylcellulose, agar bentonite and alginic acid. Suitable diluents include, but are not limited to, those which are generally useful in pharmaceutical formulations prepared using compression techniques, e.g., dicalcium phosphate dihydrate (e.g., DI-TAB®, which may be obtained from Stauffer), sugars that have been processed by cocrystallization with dextrin (e.g., co-crystallized sucrose and dextrin such as Di-Pakg, which may be obtained from Amstar), lactone, calcium phosphate, cellulose, kaolin, mannitol, sodium chloride, dry starch, powdered sugar and the like. Suitable binders include, but are not limited to, those that enhance adhesion. Non-limiting examples of such binders are starch, gelatin and sugars such as sucrose, dextrose, molasses, and lactose. Non-limiting examples of lubricants include, but are not limited to, stearates (e.g., magnesium stearate) and stearic acid.

Preferred sublingual dosage forms include sublingual tablets, creams, ointments and pastes. The tablet, cream, ointment or paste for sublingual delivery comprises a therapeutically effective amount of PYY or PYY agonist and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than 5 minutes.

Other components may also be incorporated into the sublingual dosage forms described herein. The additional components include, but are not limited to, binders, disintegrators, wetting agents, lubricants, and the like. Examples of binders that may be used include water, ethanol, polyvinyl pyrrolidone, and starch solution gelatin solution. Suitable disintegrators include, but are not limited to, dry starch, calcium carbonate, polyoxyethylene sorbitan fatty acid esters, sodium lauryl sulfate, stearic monoglyceride, and lactose. Wetting agents, if used, include glycerin, and starches. Suitable lubricants include but are not limited to, stearates and polyethylene glycol. Additional components that may be incorporated into sublingual dosage forms include those known in the art; such as those described in *Remington's, The Science and Practice of Pharmacy*, (Gennaro, A. R., ed., 20th edition, 2003, Mack Pub. Co.) which is herein incorporated by reference.

One or more of a solvent, an optional cosolvent, a hydrogel, and an oral mucosal membrane transport enhancing agent, such as those described in U.S. Pat. No. 5,284,657 (which is hereby incorporated by reference), may be included in the dosage unit form for buccal administration. The solvent may comprise from about 50 percent w/v to about 95 percent w/v or from about 55 percent w/v to about 80 percent w/v of a carrier of a non-toxic alcohol. Suitable non-toxic alcohols include, but are not limited to, ethanol, isopropanol, stearyl alcohol, propylene glycol, and polyethylene glycol (e.g., those having a molecular weight of up to about 650 daltons). Non-toxic alcohols for use in pharmaceutical formulations are well known in the art (cf., for example, Handbook of Pharmaceutical Excipients, published by the American Pharmaceutical Association and The Pharmaceutical Society of Great Britain (1986), which is hereby incorporated by reference in its entirety).

The cosolvent may be selected from water or a pharmaceutically acceptable oil. Suitable oils for use in the unit dosage form of this invention include mineral oil, Neobee™ oil, olive oil, sunflower oil, corn oil, peanut oil and the like. Hydrogels suitable for use in the dosage unit form include hydroxypropyl cellulose, hydroxypropyl methyl cellulose, sodium carboxymethylcellulose (CMC), polyacrylic acid, and poly(m-ethyl methacrylic acid).

Typically, the oral mucosal membrane transport enhancing agent facilitates the absorption of the therapeutic agent (e.g., PYY or PYY agonist) across the mucosal tissues in the oral cavity and directly into the blood stream of the subject. Suitable tissue transport enhancing agents include, but are not limited to, pharmaceutically acceptable and non-toxic essential oils, volatile oils, inorganic acids, and organic acids.

Essential or volatile oils which may be employed in the compositions include, but are not limited to, peppermint oil, spearmint oil, menthol, pepper oil, eucalyptus oil, cinnamon oil, ginger oil, fennel oil, and dill oil. The essential or volatile oil, when employed as the oral mucosal membrane transport enhancing agent in the dosage unit form may be present in a concentration ranging between about 0.5 percent w/v and about 50 percent w/v of the carrier.

Suitable inorganic and organic acids include, but are not limited to, hydrochloric acid, phosphoric acid, aromatic and aliphatic monocarboxylic or dicarboxylic acids of from two to thirty carbon atoms such as acetic acid, citric acid, lactic acid, oleic acid, linoleic acid, lauric acid, plamitic acid, benzoic acid, and salicylic acid. As used in this paragraph, the term "aromatic" carboxylic acid refers to any acid which contains the 6-membered carbocyclic ring system characteristic of benzene, and the term "aliphatic" carboxylic acid refers to any acid which contains a straight-chain or branched chain saturated or unsaturated hydrocarbon backbone.

Liquid compositions for buccal administration can be formulated into a liquid spray, a liquid drop, a gel or a paste. The desired consistency can be achieved by including in the liquid composition one or more hydrogels, substances that absorb water and produce gels of varying viscosity. Hydrogels suitable for use in pharmaceutical preparations include those known well known in the art, such as those described in *Handbook of Pharmaceutical Excipients*, supra, and *Handbook of Water-Soluble Gums and Resins*, ed. by R. L. Davidson, McGraw-Hill Book Co., New York, N.Y. (1980) (both of which are hereby incorporated by reference).

Suitable hydrogels for use in the compositions of this invention include hydroxypropyl cellulose, hydroxypropyl methyl cellulose, sodium carboxymethyl cellulose, polyacrylic acid, poly(methyl methacrylic acid) (PMMA). Preferred hydrogels are cellulose ethers such as hydroxyalkylcellulose (e.g., hydroxypropyl cellulose) and hydroxyalkylalkyl-cellulose compounds. Hydroxypropyl cellulose is commercially available in a wide range of viscosity grades sold under the tradename KLUCEL™ (Hercules, Ltd., London, England). The concentration of the hydroxyalkylcellulose is dependent upon the particular viscosity grade used and the desired viscosity of the liquid composition. For example, where the desired viscosity is less than about 1000 centipoise (cps), hydroxypropyl cellulose having an average molecular weight of about 60,000 daltons (i.e., KLUCEL EF™) can be used. Where the desired viscosity is from about 1000 to about 2500 cps, higher viscosity grades of hydroxypropyl cellulose can be used (e.g., KLUCEL EF™ and LUCEL GF™)

The dosage unit form for buccal administration may also include collagen, a water soluble additive, and/or other pharmaceutical additives, such as those described in U.S. Pat. No. 5,496,559. Collagen includes, for example, atelocollagen which is derived from a natural resource, and which is free of a telopeptide which is an antigenic portion of collagen; chemically modified atelocollagen; and naturally-occurring collagen. The collagen which has been chemically derived from the atelocollagen includes, for example, a succinylated collagen and a methylated collagen. The naturally-occurring collagen includes, for example, a collagen from a skin of bovine, a chorda of bovine, a bowel of porcine and sheep, and a human placenta. The collagen can contain a buffer, such as phosphate buffer, citrate buffer, and acetate buffer, and/or a stabilizer. Water soluble additives include for example, proteins, glycoproteins, amino acids, polyamino acids, peptides, saccharides, water-soluble polysaccharides, or a combination thereof. Proteins include, for example, gelatin and albumin. Glycoproteins include, for example, globulin. Amino acids include, for example, aspartic acid, arginine, glycine, and leucine. Polyamino acids and peptides include, for example, polyalanine, polyglycine, sodium polygultamate, sodium polyaspartate, polylysine, and polyleucine. Saccharides, polysaccharides, and water-soluble polysaccharides include, for example, fructose, sucrose, lactose, dextran, cyciodextran, mannitol, and sorbitol. A stabilizer includes one which is used for the proteinaceous physiologically active substances, such as albumin, gelatin, mannitol, and trehalose. Suitable preservatives include, but are not limited to, p-hydroxybenzoates, sorbic acid, and salicylic acid. Suitable buffers include, but are not limited to, citrate buffer, acetate buffer, and phosphate buffer. Suitable sweeteners include, but are not limited to, mannitol, glucose, maltose, starch, and lactose.

Suitable flavors include, but are not limited to, aspartic acid, citric acid, and lactic acid. Suitable binder include, but are not limited to, methylcellulose, ethylcellulose, and carboxy methyl cellulose. Suitable suspending agents include, but are not limited to, Tween 20 and Tween 80. Suitable disintegrators include, but are not limited to, glycerol and starch.

Dosage unit forms for buccal administration may be in the form of a hard candy (e.g. lollipops and mints) or a film, e.g., a slow dissolving film or a fast dissolving film (such as that described in U.S. Pat. No. 6,596,298, which is hereby incorporated by reference). Such films can be prepared by including a film forming agent in the dosage unit form. Suitable film forming agents include, but are not limited to, those described in U.S. Pat. No. 6,596,298 (e.g., pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. According to one embodiment, the concentration of film forming agent in the dosage unit form ranges from about 0.01 to about 99 wt %, from about 30 to about 80 wt %, from about 45 to about 70 wt %, or from about 60 to about 65 wt % (based upon 100% total weight of the film). Administration compositions can also take the form of a pouch that can be placed next to the cheek, or between the lower teeth and lip, similar to smoke-less tobacco products.

The compounds and compositions of the subject invention are useful for administering biologically or chemically active agents to any animals, including but not limited to birds such as chickens; fish, reptiles, mammals, such as rodents, cows, pigs, dogs, cats, primates, and particularly humans, and insects.

EXAMPLES

The following examples illustrate the invention without limitation. All parts are given by weight unless otherwise indicated.

Example 1

Buccal Deliver of $PYY_{[3-36]}$ in Beagle Dogs

About 1 mg of PYY solid powder was gradually added and blended with about 100 mg Delivery Agent (SNAD). Upper punch, lower punch and die of Carver 4350 manual pellet press with a Caplet shape model sold by Natoli Engineering Company, Inc. were treated with magnesium stearate (0.1%). About 101 mg of mixed powder was fed into the die and a mini bead shape tablet was made at about 1000 PSI. The resulting solid dosage form was about 5 mm diameter and about 1 mm in height.

Two male and two female Beagle dogs weighing between 10.2 and 12.7 kg were fasted overnight before the experiments. The animals were moderately sedated using 0.4-0.8 mg/kg midazolam and 0.03-0.04 mg/kg medetomidine. Once sedated, an intravenous catheter was placed on the cephalic vein for blood sampling.

The solid dosage form was placed under the dog's tongue. To facilitate the dissolution of the tablet, about 0.75 ml of saline solution was infused slowly under the tongue on the right side and another 0.75 ml on the left side. One hour post-administration, any remaining formulation was removed by syringe aspiration and the sublingual area was rinsed once with saline solution, removing it afterwards by syringe aspiration.

Blood samples (about 0.5 ml) were collected serially from the cephalic vein, typically at time=0 (predose), 15, 30, 45, 60, 90, 120, 150, and 180 minutes post dose. The samples were placed in serum separating tubes and left at room temperature for 30-45 minutes to allow clotting. The samples were then centrifuged at about 2-8° C. for 10 minutes at 2500 rpm. The resulting serum was transferred into a tube and placed on dry ice and then stored frozen at −70±10° C. until assayed. Serum PYY concentrations were quantified using a PYY[3-36] radioimmunoassay (Catalog #RK-059-02 from Phoenix Pharmaceuticals, Inc., Belmont, Calif.). Results from the animals in each group were averaged for each time point. The results (±standard error) are shown in FIG. 1.

Any information regarding specific mechanism(s) is provided for only background purposes. The invention should not be construed to be limited, in any way, by any description of the mechanism(s) by which the delivery agents or active agents (e.g., PYY, PYY agonists) may function.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

We claim:

1. A method for buccally administering an effective amount of peptide YY or the peptide YY agonist PYY[3-36], or a mixture thereof, to a patient in need thereof, comprising the step of buccally administering a solid dosage unit form comprising (a) at least one peptide YY, the peptide YY agonist PYY[3-36], or a mixture thereof, and (b) a delivery agent selected from N-(8-[2-hydroxybenzoyl]-amino)caprylic acid, N-(10-[2-hydroxybenzoyl]-amino)decanoic acid, and pharmaceutically acceptable salts thereof.

2. A method of treating obesity in a patient in need thereof, comprising the step of administering to the patient an effective amount of the dosage unit form of claim 1.

3. The method of claim 1, wherein the delivery agent is selected from the monosodium salt of N-(8-[2-hydroxybenzoyl]-caprylic acid, the monosodium salt of N-(10-[2-hydroxybenzoyl]-amino)decanoic acid, the disodium salt of N-(8-[2-hydroxybenzoyl]-amino)octanoic acid, and the disodium salt of N-(10-[2-hydroxybenzoyl]amino)decanoic acid.

4. The method of claim 1, wherein the delivery agent is N-(8-[2-hydroxybenzoyl]-amino)caprylic acid or a pharmaceutically acceptable salt thereof.

5. The method of claim 1, wherein the delivery agent is N-(10-[2-hydroxybenzoyl]-amino)decanoic acid or a pharmaceutically acceptable salt thereof.

6. The method of claim 1, wherein the solid dosage unit form is a tablet, a capsule, a particle, a powder or a sachet.

7. The method of claim 1, wherein the dosage form comprises 100 mg of N-(10-[2-hydroxybenzoyl]-amino)decanoic acid or a pharmaceutically acceptable salt thereof, and 1 mg of PYY[3-36].

* * * * *

SEQUENCE LISTING

```
<160> NUMBER OF SEQ ID NOS: 2

<210> SEQ ID NO 1
<211> LENGTH: 36
<212> TYPE: PRT
<213> ORGANISM: Homo sapiens

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

```
<210> SEQ ID NO 2
<211> LENGTH: 34
<212> TYPE: PRT
<213> ORGANISM: Homo sapiens

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```